United States Patent [19]

Metzger et al.

[11] Patent Number: 4,925,628
[45] Date of Patent: May 15, 1990

[54] SAMPLE PREPARATION CHAMBER WITH MIXER/GRINDER AND SAMPLE ALIQUOT ISOLATION

[75] Inventors: Andre Metzger, Le Verger, France; Peter Grimm, Frenkendork, Switzerland; Andre J. Nohl, Menlo Park; Vance J. Nau, Cupertino, both of Calif.

[73] Assignee: Ciba-Geigy Corporation, Ardsley, N.Y.

[21] Appl. No.: 70,759

[22] Filed: Jul. 7, 1987

Related U.S. Application Data

[63] Continuation-in-part of Ser. No. 942,198, Dec. 16, 1986.

[51] Int. Cl.$^5$ .............................................. G01N 1/10
[52] U.S. Cl. ..................... 422/100; 422/68.1; 422/101; 422/102; 422/103; 436/18; 436/54; 436/179; 436/180; 366/65; 366/169
[58] Field of Search ............... 422/99, 100, 101, 102, 422/283, 68, 103; 436/54, 18, 174, 179, 180; 366/64, 65, 168, 270, 169

[56] References Cited

U.S. PATENT DOCUMENTS

| | | |
|---|---|---|
| 3,223,485 | 12/1965 | Ferrari et al. . |
| 3,223,486 | 12/1965 | Holl, Jr. et al. ................ 422/82 X |
| 3,259,743 | 7/1966 | Pick et al. . |
| 3,511,618 | 5/1970 | Michaud et al. ................ 422/283 X |
| 3,583,232 | 6/1971 | Isreeli et al. . |
| 3,594,129 | 7/1971 | Jones et al. . |
| 3,929,411 | 12/1975 | Takano et al. . |
| 4,036,590 | 7/1977 | Helder et al. . |
| 4,219,530 | 8/1980 | Kopp et al. . |
| 4,252,769 | 2/1981 | Hood et al. . |
| 4,325,910 | 4/1982 | Jordon . |
| 4,416,764 | 11/1983 | Gikis et al. ..................... 422/283 X |
| 4,520,108 | 5/1985 | Yoshida et al. . |
| 4,545,957 | 10/1985 | Vanhumbeeck et al. ............ 422/81 |
| 4,585,623 | 4/1986 | Chandler ........................ 422/103 X |
| 4,677,077 | 6/1987 | Onizuka et al. ................. 436/175 X |

FOREIGN PATENT DOCUMENTS

| | | |
|---|---|---|
| 0089937 | 9/1983 | European Pat. Off. . |
| 2331010 | 6/1977 | France . |
| 2579749 | 3/1985 | France . |
| 56-2560 | 1/1981 | Japan . |

*Primary Examiner*—Barry S. Richman
*Assistant Examiner*—Lynn M. Kummert
*Attorney, Agent, or Firm*—Ciotti & Murashige, Irell & Manella

[57] ABSTRACT

There is disclosed a sample preparation chamber for a system for preparing samples of various compositions for assay by liquid chromatography. The sample preparation chamber is includes a container having a threaded cap and a threaded, lightweight, translucent plastic cup. A stirrer/grinder shaft driven by a motor and connected to a propeller/grinder passes through the cap. The cup has a sloped bottom with a sump region, and a fill/empty pipe passes through the cap and has its outlet at or near the sump. A nozzle/fill pipe arrangement allows the walls to be washed down as liquid is pumped into the cup. A second fill pipe with its outlet spaced up from the bottom of the cup is also used, and a sample metering valve having an inlet in said cup is present. The sample metering valve is used to isolate a known volume of the sample from the rest of the sample for release back into the cup after the remaining sample has been pumped to waste for purposes of diluting the known volume of sample to a known concentration.

16 Claims, 6 Drawing Sheets

SAMPLE PREPARATION CHAMBER WITH MIXER/GRINDER AND SAMPLE ALIQUOT ISOLATION

This is a continuation-in-part application of U.S. patent application "Sample Preparation Chamber With Mixer/Grinder and Sample Aliquot Isolation", Ser. No. 942,198, filed 12/16/86, now co-pending.

BACKGROUND OF THE INVENTION

The invention relates to the field of sample preparation systems for chemical assays, and, more particularly, to the field of sample preparation chambers or systems that are adapted to handle liquid, solid, granulated or highly viscous samples.

In many chemical processing facilities and laboratories there is a need to do chemical assays on chemical samples. Often these assays are done by means of gas or liquid chromatography. The form in which the samples for analysis come are many and varied. For most chromatography assays, diluted solutions of a homogeneous mixture of the sample and a diluent must be used. If the sample is a solid, it must first be dissolved. If the sample is a two phase liquid/liquid or liquid/solid combination, the mixture must be homogenized. If the sample is viscous, its viscosity must be reduced by dilution so that it may be pumped through the liquid chromatography column. All the samples must be diluted to a known concentration prior to pumping the diluted sample solution through the liquid chromatography column.

It is important in preparing samples for liquid chromatography and other types of assays to know the exact concentration of the sample being supplied to the assay. When dilution is being performed therefore, it is important to be able to isolate a known quantity of the sample. If the same container is to be used for a series of dilutions, it is also important to remove the rest of the sample from the container where the diluted sample is to be stored. To get exact concentrations, it is also necessary to be able to wash out the remnants of the sample from the various tubes in the system and off the walls of the sample container.

For solid samples it is important to be able to grind them to powder and to be able to add solvent to the powder before dissolving it in preparation for dilution to the desired concentration. For two phase samples it is advantageous to be able to use the same mechanism used for the grinding of the solid samples to mix the two phase samples to homogenize them.

Further, for any samples, particularly solid or viscous samples which are too viscous to pump, it is useful to have a sample container that is lightweight, detachable and portable so that it may be taken to the location of the sample and sample may be placed therein. The sample amount may be determined by weighing the cup before and after the sample has been placed therein. The sample container may then be filled with diluent to reduce the viscosity to a useable range.

The prior art sample preparation systems do not have all the capabilities noted above. Basically, the prior art sample preparation systems are designed to handle only ideal samples which are homogeneous liquid. The ability to handle two phase samples, solid samples or very viscous samples has, heretofore been missing from the art. Further, prior art sample preparation chambers do not include means to wash down the walls of the chamber prior to diluting the metered sample, or to isolate a fixed amount of sample immediately following homogenization.

SUMMARY OF THE INVENTION

According to the teachings of the invention there is provided a sample preparation chamber which is capable of being used to prepare many different types of samples for chemical assay, especially by liquid chromatography. The sample preparation chamber is comprised of a threaded, sloped bottom cup which is lightweight and transparent for holding and transporting the sample liquid or solid. The cup threads to a cap which serves to keep liquids in by a liquid seal between the cup flange and the mating cap flange. The detachability of the cup allows the cup to be removed and taken to the location of the sample so that a measured amount of sample may be placed therein if desired. Several elements pass through the cap. These elements include a drain pipe which extends to the lowest point in the sloped bottom of the cup and has a diameter which is large enough to pump viscous liquids through without excessive pressure. A second fill pipe also passes through the cap, but does not extend to the bottom of the cup. This fill pipe may be used to pump liquid sample, solvents or diluent into the cup as may the larger fill pipe that extends to the bottom of the cup.

There is also a nozzle which extends through the cap which may be used to wash down the side walls of the cup. The nozzle is a propeller like structure in line with the fluid outlet of a pipe. To use this feature, the user pumps solvent or some other liquid through the pipe connected to the nozzle. The fluid flow causes the propeller or nozzle element to spin. This deflects fluid laterally out toward the side walls of the cup thereby washing down the walls.

The sample container also includes a stirring/grinding mechanism. This mechanism includes a motor driving a shaft which passes through the cap. The shaft is coupled to a propeller or other stirring structure which may or may not be suitable for grinding solid samples. The user may change the structure of the stirrer/grinder propeller to best suit the types of samples the user customarily prepares for assay. For some applications the user may prefer to substitute other types of mixers, such as ultrasonic mixers or high speed mixers both of which are commercially available.

A sample metering valve is also provided for allowing the user to isolate a known volume of sample from the rest of the material in the cup. This known volume may then be released back into the cup after the rest of the sample has been pumped to waste and, optionally, the walls have been washed down and the solvent pumped to waste.

DETAILED DESCRIPTION OF THE PREFERRED EMBODIMENT

Figure 1:
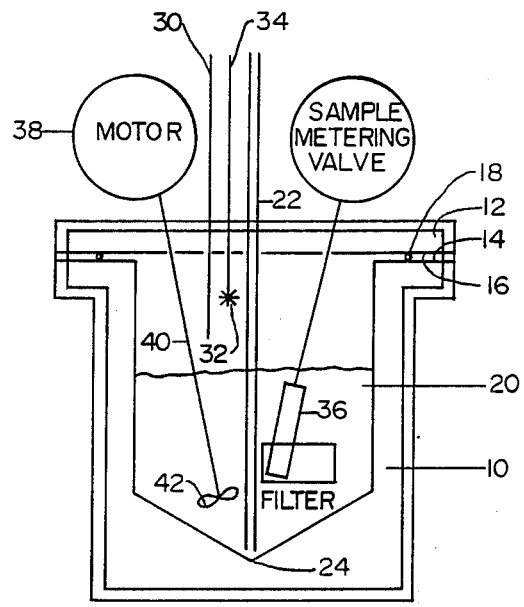
FIG. 1 is an elevation view of the sample container system of the invention.

FIG. 1 is an elevation view of the sample container system of the invention. The sample container is generally used as part of a sample preparation system which uses a pump capable of highly accurate delivery of fluid volumes. The sample container includes a cup 10 which, in the preferred embodiment, is made of a transparent or translucent, lightweight, chemically inert material. Depending upon the user's application, the cup may be made out of other materials as well where one or more of the above properties is not important. The cup is threaded or otherwise formed so that it may be mechanically attached to and supported by a cap 12. Typically, the cap will be attached to some solid support in the system, and will have a matching means of mechanical attachment to the cup. The manner of attachment to the cup is not critical to the invention, and any mechanical linkage which will withstand the weight and provide a seal which is adequate for the user's application will suffice.

The cup and the cap are shown in FIG. 1 as having mating surfaces 14 and 16 and a seal 18. The seal 18 may be any type of seal which will maintain the liquid 20 in the cup, or optionally may be omitted in some applications. Further, other designs may be used for sealing the structure in that mating surfaces 14 and 16 may be in the form of a tongue in groove seal or any other known structure.

The cup may have any thickness which will provide adequate structural strength for the sample types and application contemplated by the user. For a general purpose system where samples of many types are to be handled including solids, the cup 10 should have sufficient structural strength to withstand the forces which are involved in grinding a solid sample into a powder or smaller chunks in a dry state prior to the addition of solvent to dissolve the sample. A disposable version of the cup may be used where the cup consists of a thin disposable lining supported by a secondary stronger retaining structure. The bottom of the cup has a sump or lowest point where the last drops of a liquid collect. The exact configuration of the bottom is not critical as long as there is a lowest point 24 from which the liquid in the cup may be collected for pumping to waste. It is important to be able to pump as much as possible of the remaining sample out of the cup after the desired aliquot of sample has been isolated by the sample metering valve to be described below. This allows the final concentration of the sample to be closely controlled, by allowing the user to drain out all remaining sample before releasing the isolated, known volume of sample from the metering valve into the cup 10 and pumping in a known amount of diluent. If some unknown amount of sample was in the bottom of the cup which was not susceptible to being drained out or rinsed out because of the shape of the bottom of the cup, then the final concentration could not be controlled with good accuracy.

Figure 2:
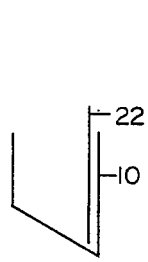
FIG. 2 shows in elevation and cross section the configuration of another shape for the cup bottom with the lowest point along an edge of the cup.
Figures 3, 4:
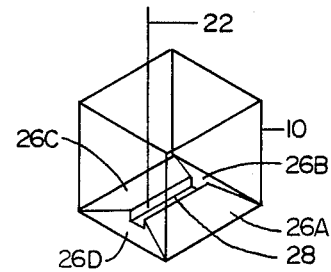
FIG. 3 shows another shape for the bottom of the cup wherein a sump is centrally located with sloping bottom panels converging on the sump.
FIG. 4 shows another shape for the bottom of the cup wherein a slot is formed in the bottom of the cup with sloping bottom panels converging on the slot with the bottom of the slot being the lowest point of the bottom.

FIGS. 2 through 4 show some of the other possible bottom shapes for the cup 10. FIG. 2 shows, in elevation and cross section, one possible embodiment for the shape of the bottom of the cup. In this embodiment, the cup will have at least one straight edge and the lowest part of the bottom will be adjacent to this edge. The bottom of the cup slopes toward the low point adjacent to the straight edge. The other sides of the cup may have any desired shape. For that matter, the "straight" edge need not be straight at all, but, instead, may be wavy or curved. FIG. 3 shows in cross section and elevation another possible bottom configuration for the cup 10 using a well or sump in a sloped bottom where the bottom panels all slope toward the well. The cup may be cylindrical, curved, a polygon or rectangular for the embodiment of FIG. 3. The sump 24 may be round, curved, polygonal or rectangular. FIG. 4 shows in perspective another bottom configuration for the cup 10. In this embodiment, the bottom panels 26A through 26D all slope toward a slot 28 formed in the bottom. The slot 28 serves as a sump and the bottom of the slot is the lowest part of the bottom. Alternatively, a flat bottom cup could be used with the cup tilted on its side so that the bottom corner of the cup which is lowest could serve as the sump.

A fill/drain pipe 22 of relatively larger diameter passes through the cap 12 and extends down into the cup such that the opening of the fill/drain pipe is at or near the lowest point in the bottom. Preferably, the fill pipe opening is located as near as possible to the lowest point of the bottom to maximize the amount of sample which can be pumped out of the cup. The purpose of the larger diameter fill/drain pipe 22 is to allow the cup 10 to be emptied as quietly as possible and to allow heterogeneous slurries or viscous samples to be pumped into or out of the cup. In the preferred embodiment, there is a seal (not shown) around the fill/empty pipe where it passes through the cap 12.

Another fill pipe 30, which may be a smaller diameter than the fill/empty pipe 22, is provided to allow the user to pump in sample or diluent which is not so viscous as to hinder the process of pumping it through a small diameter tube. The fill pipe 30 does not extend all the way down to the bottom of the cup, but stops short of the bottom, and may be used to selectively sample a particular layer of a multiple phase system.

A nozzle 32 and fill pipe 34 together comprise the system which provides the ability to wash down the walls of the cup. When a viscous sample or any sample has been present in the cup and pumped or otherwise driven out to waste, resident sample or sample solution sticks to the walls of the cup.

Any residual sample adhering to the cup or tubing walls presents a source of contamination to the next step of the sample preparation process or the next sample processed and must therefore be removed. More specifically, the unknown residual sample or sample solution would present a source of contamination from one sample to the next, and a source of cumulative error when using the same vessel for successive sample prep steps.

To minimize the uncertainty created by the above situation, the nozzle 32 and fill pipe 34 are used. A suitable solvent which can dissolve the sample in question from the walls is pumped in via the pipe 34. This stream of solvent leaving the end of the fill pipe attached to the nozzle 32 causes the nozzle 32 to spin due to torsional forces present from the design of the nozzle 32. That is, the nozzle is shaped such that the force of liquid exiting in one direction off center from the main axis causes the nozzle to spin in the opposite direction. When the stream of solvent is forced through the nozzle, the nozzle spins thereby throwing solvent laterally against the walls of the cup. This washes down the walls of the cup to remove remaining sample stuck thereto. The solvent and remaining sample so removed and in solution in the solvent are then pumped to waste using the fill/empty pipe 22.

To provide a facility to mix two phase solvents, to grind solid samples to powder or smaller chunks, and to speed up the process of dissolving such samples in solvent, a mixer/grinder 38 is provided. This device includes a motor or other type of device capable of imparting a mixing action on the sample or sample solution. Such other types of devices include pneumatic motors, high speed mixers, ultrasonic probes, etc. The mixer/grinder 38 uses a propeller/grinding tool 42 attached to the end of the shaft 40 to do the mixing of liquids and the grinding of solid samples. The applicants believe that the invention may be the first general purpose sample preparation for liquid chromatography designed to allow processing of solid samples, slurries, or two phase liquid samples prior to the addition of solvent in order to put the sample in a solution suitable for passing through a liquid chromatography column. The user may use any type of mixer/homogenizer design which suits the type of samples the user normally processes. Designs for propellers and grinders which are suitable for various situations are known although they may be in other art areas. There is an optional seal (not shown) in the cap 12 through which the shaft 40 passes to maintain the liquid tight integrity of the sample preparation chamber during the turbulence created by the mixer/grinder 38. The design for such a seal is well known in the art.

To provide a facility for the taking of sample aliquots of known volume, there is a sample metering valve 36. This apparatus can take many forms some of which are more suitable for certain types of samples than others. The details of the different types of sample metering valves which are suitable for various types of samples are given in U.S. patent application entitled, "Sample Metering Valve for Sample Preparation System", Ser. No. 942,201, filed 12/16/86 assigned to the assignee of the present application, said application being hereby incorporated by reference. For completeness here, there will be given a description of two types of sample metering valves which are acceptable to practice the invention.

Figure 5:
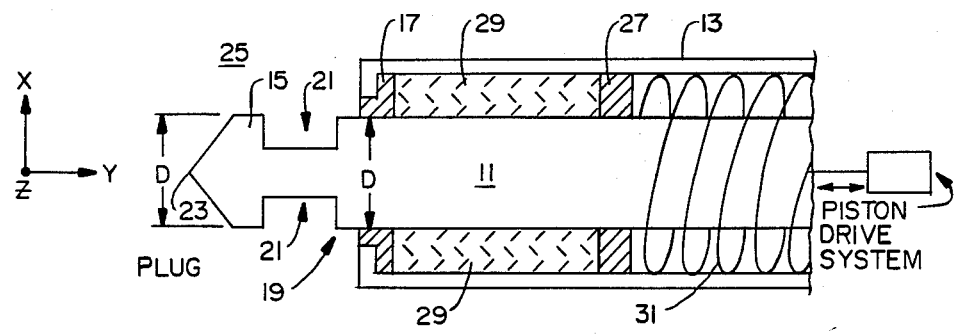
FIG. 5 is a cross sectional view of a sample metering valve for handling liquid samples and shown in the piston extended position.

Referring to FIG. 5, there is shown a cross sectional view of the sample metering valve of the preferred embodiment. A piston 11 is disposed within an open ended cylinder 13. The piston is typically metal with a chrome finish or is highly polished so as to have a smooth surface to minimize friction as the piston moves back and forth on the y axis. The piston has a T shaped end with a sealing plug 15 which has the same outside diameter D as the inside diameter of a seal 17 at the "open" end 19 of the cylinder. The piston 11 is shown in the extended position. In the retracted position of the piston 11, shown in FIG. 6, the sealing plug 15 is pulled back into the opening in the cylinder 13 so as to be in sealing contact with the sealing ring 17.

The piston 11 has a sample collecting recess 21 formed therein a small distance along the y axis away from the tip 23 of the piston. The purpose of the sample collecting recess 21 is to capture a known volume of material from the surrounding medium 25 when the piston is in the extended position. Therefore, the recess 21 must be machined or otherwise formed to be of a known volume and must be placed on the piston 11 and sized so as to be at least partially exposed to the surrounding medium 25. Preferably, the recess 21 will be placed and sized so as to be completely exposed to the surrounding medium 25 when the piston is in the extended position as shown in FIG. 5. The piston may be formed of other materials than metal such as teflon or other plastic materials. This is true of the cylinder 13 also. The caveat on material selection is that the materials selected for any component of the valve must be compatible with the intended environment in which the valve is to be used so that the environment will not adversely affect the materials and cause a valve failure. This is particularly true in sampling of process streams.

A significant improvement over the prior art for the valve of FIG. 5 resides in the sealing structure. This structure has no dead volume or recesses which can inadvertently collect unknown volumes of sample when the piston is in the extended position. This accomplished by the elimination of multiple O-rings for sealing and substitution of a flexible, self compensating sealing arrangement using the property of cold flow of malleable materials to adjust for differences in dimensions of the various components with variations in temperature. The sealing structure is comprised of two sealing rings 17 and 27 of relatively harder materials with a smaller creep rate (non-recoverable strain or permanent percentage deformation or cold flow) separated by and in abutting contact with a cylindrical seal 29 of malleable material of a relatively faster creep rate. A spring 31 applies a constant force to the upper sealing ring 27 biasing it to move toward the sealing ring 17 thereby putting the sealing cylinder 29 in compression stress. This causes the sealing cylinder 29 to attempt to cold flow, i.e., expand in whatever direction is available for expansion in response to the compression stress. If there is any gap between the sidewalls of the piston 11 and the cylindrical seal 29, the cold flow results in radial strain in the cylindrical seal 29 which reduces or eliminates the gap thereby effecting a good seal. Changes in temperature which alter the diameters of the piston 11 and the cylinder 13 (possibly differentially) will not adversely affect the integrity of the seal. This follows because the cold flow strain adjusts for any temperature induced changes in gap size since the pressure exerted by the spring 31 is substantially constant regardless of temperature. Substantially less cold flow in the sealing rings 17 and 27 results because of their relatively harder constitution.

No dead space results in the sealing structure of the invention since there are no gaps between the sealing rings 17 and 27 and the cylindrical seal 29. Further, the seals are affixed to the cylinder and not to the piston, so the seals never are moved by the piston out into the surrounding medium. No spurious, unknown quantities of sample can be accumulated by the seals because of this structure.

The apparatus to move the piston may be any known force producing apparatus such as pneumatic or electrical devices. It is not necessary in the preferred embodiment to know exactly how far the piston moves since the the sample volume is fixed in the recess 21. It is only necessary to know that the piston has been moved to its extended position or to its retracted position.

In the preferred embodiment, the sealing rings 17 and 27 are teflon impregnated with glass, graphite or some other material which makes the teflon harder than pure teflon. The sealing cylinder 29 is pure teflon, and has a higher degree of deformability than the sealing rings 17 and 27. These material selections are not critical to the invention however, and any material which is chemically inert, has a low coefficient of friction and which can cold flow will be acceptable for the sealing cylinder 29. The same is true for the material selection of the sealing rings 17 and 27 except that the material must be relatively less deformable than the sealing cylinder 29, or must be capable of being made so with suitable alloying or other techniques.

Figure 7:
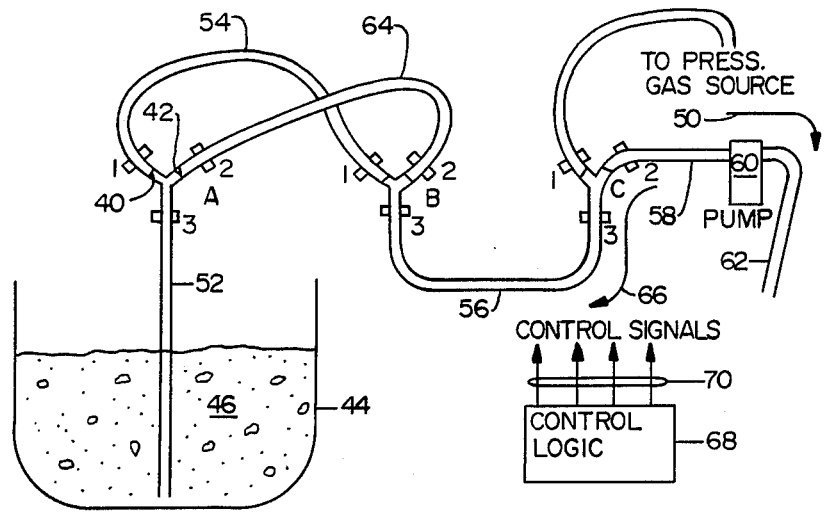
FIG. 7 is a diagram of another, preferred embodiment for a sample metering valve for handling slurry type samples with entrained gas bubbles.

FIG. 7 shows the preferred embodiment for the sample metering valve for slurry or other samples where the volume consumed by gas bubbles is to be eliminated or minimized to improve the accuracy of the volume of the isolated sample. The sample metering valve is actually comprised of three, three-way valves labelled A, B and C in FIG. 7. Each three-way valve is a Y connection with a valve gate such as the gates 40 and 42 in valve A, and each valve A through C has three ports labelled 1 through 3. The gate valves in each valve operate so that at any particular time only one of ports 1 or 2 is coupled to port 3. The connections are as shown in FIG. 7 for the sample metering valve of the preferred embodiment.

The operation of the system to take a sample is as follows. A sample cup 44 is filled with sample 46. Ports 1 on valves A and B are then activated (opened). and port 2 of valve C is activated. A sample pump coupled to port 2 of valve C is then turned on to pump liquid in the direction of arrow 50. This draws sample up into the fill tube 62 and through ports 3 and 1 of valve A, pipe 54, ports 1 and 3 of valve B, pipe 56, ports 3 and 2 of valve C, pipe 58, pump 60 and empty pipe 62. In alternative embodiments, any pumping mechanism or system may be used, as long as the loop is completely filled.

The pump 60 must be pumped long enough to completely fill the pipe 54 and at least partially fill pipe 56 with enough sample such that when the sample is compressed, the pipe 54 remains filled to capacity. The sample chamber of known volume in the embodiment of FIG. 7 is the pipe 54 plus whatever volume exists in the valves A and B up to the valve plates.

After filling the sample chamber, valve A, port 2 is activated to trap the sample in the pipe 54, and valve C, port 1 is activated to couple pressurized gas into pipe 56. This pressurizes the liquid and gas in the pipes 56 and 54 and thereby compresses any gas bubbles in the pipes 54 and 56 down to zero or small volume. The volume of material in the sample chamber is substantially all liquid by virtue of this pressurization of the lines. Next, valve B, port 2 is activated thereby isolating the sample in the sample chamber 54 between valves A and B. The pump 60 is then activated to pump the remaining sample 46 in the sample cup and any remaining untrapped sample in pipe 56 out of the system through pipe 62. That is, sample is pumped up through fill pipe 52, ports 3 and 2 of valve A, pipe 64, ports 2 and 3 of sample valve B, pipe 56, ports 3 and 2 of valve C, pipe 58, pump 60 and out pipe 62.

Pipe 62 in the preferred embodiment may be coupled alternately to a source of solvent and to a waste dump. Valve C port 2 is reactivated and the pump 60 is then activated to pump solvent in the direction of the arrow 66 to flush out the pipes 56, 64 and 52 and to wash out the remaining sample from the sample cup 44. The pump 60 is then reversed to pump out the solvent in the system and the sample cup in preparation for the dilution.

Next, ports 1 of valves A and B are activated, and the pump 60 is activated to pump in the desired amount of diluent to get the desired sample to diluent concentration. The diluent pumped in in the direction of the arrow 66 flushes the trapped sample out of the pipe 54 down into the sample cup 44. Since the volume of trapped sample is relatively precisely known, good accuracy of the sample concentration may be obtained. Serial dilutions are also possible by repeating the above steps several times to get successively weaker concentrations.

Control logic 68 supplies control signals to all valves and the pump 60 via control bus 70. The control logic 68 may be a programmed digital computer, dedicated combinatorial logic or any other circuit which can cause the above identified algorithm to work. The details of such logic will be apparent to those skilled in the art given the above description of how the system is supposed to operate, and no further details will be given here. The particular control logic used in the preferred embodiment is described in co-pending U.S. patent application "Control System for a Sample Preparation System" by Vance Nau and Keith Grant, Ser. No. 942,196, filed 12/16/86 which is hereby incorporated by reference.

Figure 6:
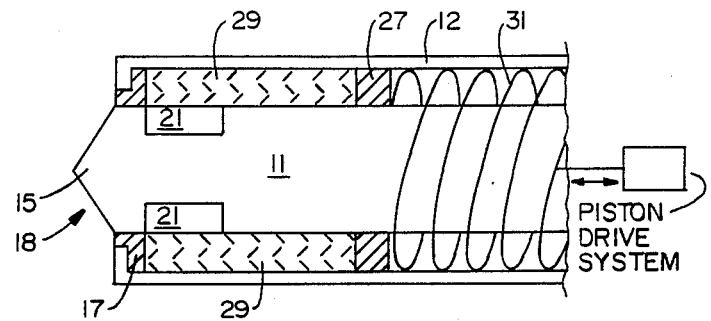
FIG. 6 is a cross sectional view of the sample metering valve of FIG. 5 and shown in the piston retracted position.
Figure 8:
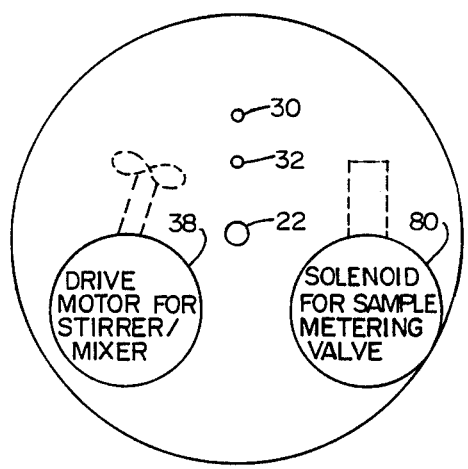
FIG. 8 is a top view of the sample preparation container of FIG. 1.

FIG. 8 is a top view of the sample preparation chamber of FIG. 1 with a round shape assumed. The view of FIG. 8 assumes that a sample metering valve of the type shown in FIGS. 5 and 6 is being used, and that a solenoid 80 is being used to drive the piston 11 in the cylinder 13 of the sample metering valve. The relative arrangement of the various elements of the system are not critical to the practice of the invention, and the arrangement of FIG. 8 is exemplary only.

Figure 9:
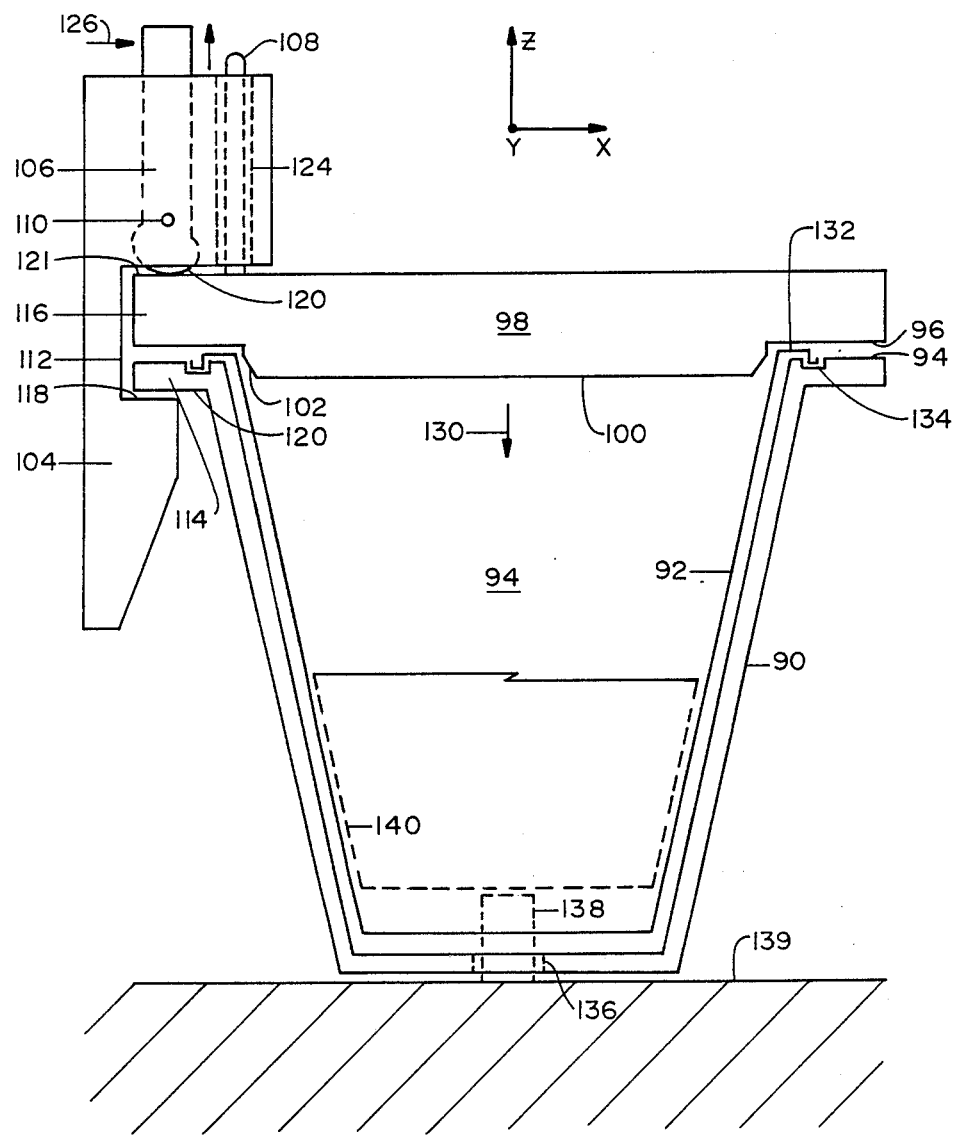
FIG. 9 is an elevation view of the configuration of the sample chamber in more detail showing the details of the removable cup and the stainless steel shell which provides support for the removable cup and showing the details of the sealing mechanism.

Referring to FIG. 9, there is shown an elevation view of the sample chamber details and the details of the sealing mechanism. The sample chamber is made up of a stainless steel shell 90 which provides support for a removable plastic cup 92. The plastic cup is removable from the steel shell and provides a chamber 194 in which sample materials are stored during the grinding, mixing, dilution and other processes of sample preparation. The stainless steel shell 90 has a flange having a flat surface 94 which mates with a corresponding flat surface 96 on the underside of a mating flange on a lid 98. The underside of the lid 98 has a raised, cylindrical shaped plateau 100. The cylindrical edge of the plateau has a bevel 102 which is forced against the plastic of the wall of the cup 92 when the lid 98 is forced downward by the bayonet clamping mechanism 104.

In the preferred embodiment, the bayonet clamping mechanism is comprised of a latch piece 104, a camming lever 106 and a slide bearing 108. The camming lever 106 is rotatably coupled to the latching mechanism 104 by a pin 110. The latch mechanism 104 has a notch 112 formed therein which receives the flanges 114 and 116 of the stainless steel cup 90 and the lid 98, respectively. A bottom surface 118 of the notch 112 fits under the bottom surface 120 of the flange 114. The latch 104 has a clearance hole 124 formed therein in which a pin 108 forming the shaft of the slide bearing fits. There are two such pins and clearance holes coupling the latch 104 to the lid 98. These pins and clearance holes allow the latch 104 to slide vertically along the z axis under the influence of the camming action of the camming lever 106.

The camming lever 106 has a cam surface 120 which bears upon the upper surface 121 of the flange 116 of the lid 98. The shape of the cam 120 is such that when the lever 106 is pushed by the force represented by vector 126, the lever 106 rotates clockwise about the pin 110 thereby causing the cam surface to rotate and push the latch 104 upward along the positive z axis relative to the lid 98. This pulls the cup 90 upward by the force applied by the surface 118 against the undersurface 120 of the cup flange 114. As a result, the lid 98 and the cup 90 are forced together causing the relative movement of the lid 98 downward along the negative z axis as shown at 130. This causes the beveled surface 102 of the lid 98 to squeeze the plastic cup 92 to the inside wall of the stainless steel cup 90 thereby forming a seal.

In the preferred embodiment, the plastic cup 92 has a lip 132 formed circumferentially around the top of the cup. This lip engages a groove 134 formed in the top surface 94 of the cup flange 114 such that the cup 92 is suspended from the groove 134. The plastic cup's depth in the negative z direction is less than the same dimension for the stainless steel cup 90. In some embodiments, this suspension aspect of the invention may be eliminated, and the cup 92 may be made of such a dimension that the cup 92 fits snugly within the cup 90 such that the top edge 132 (without a lip) of the plastic cup reaches the level of the top surface 94 of the flange 114. This is necessary so that the beveled surface 102 of the lid 98, when it is in its sealed position, will pinch the plastic of the cup 92 to the inner wall of the stainless steel cup 90. It is important to control the dimensions of the plastic cup 92 such that the top of the cup 132 does not protrude so much above the level of the surface 94 as form an obstruction to squeezing together of the circular flange surfaces 96 and 94.

The stainless steel cup 90 also has a hole 136 formed in the bottom thereof. The purpose of this hole is to allow a pin 138 attached to a stable surface 138 to enter the stainless steel cup 90 and contact the bottom surface of the plastic cup 92 when the cup assembly has the lid removed. This raises the plastic cup 92 to the position shown in phantom at 140. This facilitates removal of the plastic cup 92 from the stainless steel cup 90.

It is not necessary that the cup 90 be stainless steel although this is preferred for corrosion purposes. The cup 90 may be made of any material that provides sufficient rigidity to allow the above described sealing action to occur. The diameter dimensions of the cup 90 and the plateau 100 must be controlled sufficiently so that the beveled surface will be sufficiently close to the inside wall of the cup 90 when the bayonet latch mechanism is in the sealed position with flange surfaces 94 and 96 pinched together such that the plastic of the cup 92 is sufficiently pinched between the beveled surface and the inside wall of the cup 90 to form a seal.

Figure 10:
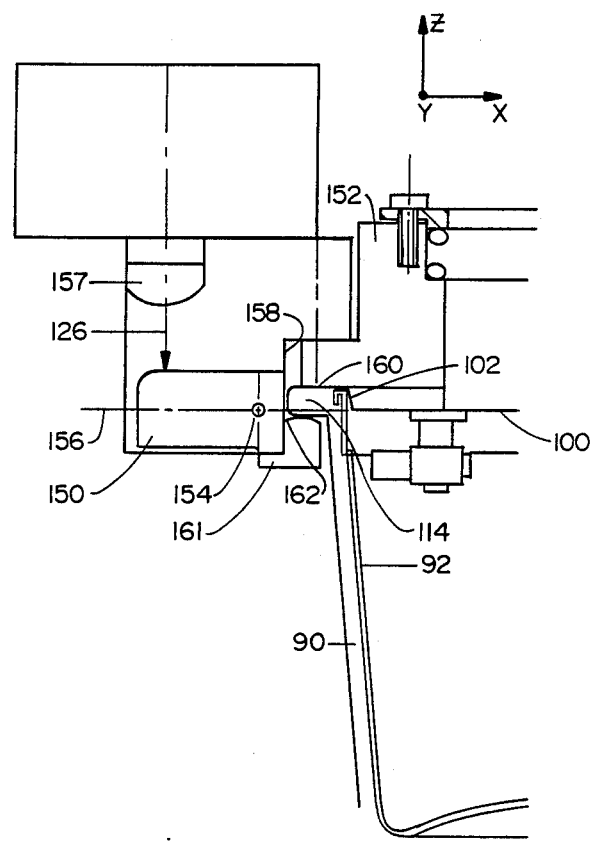
FIG. 10 is an elevation view of a second embodiment of the latching mechanism to form a seal between the cup lip and the lid.
Figure 11:
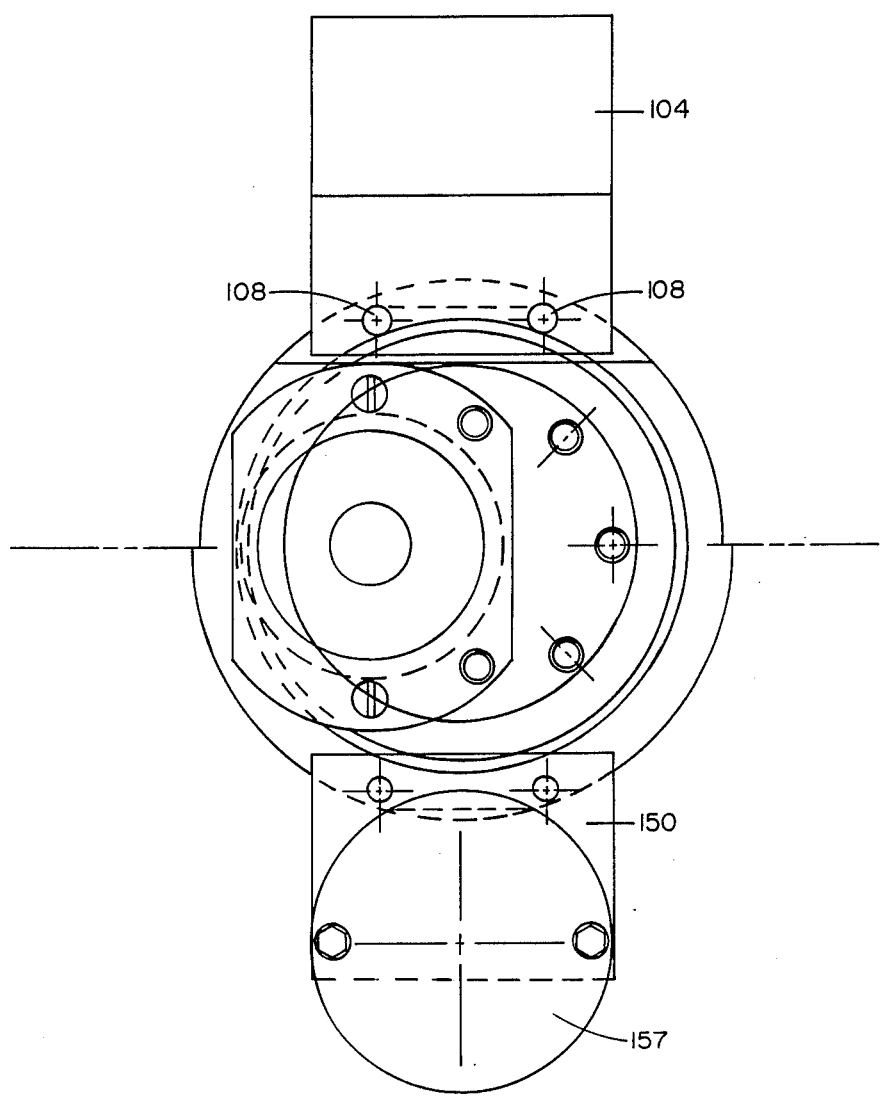
FIG. 11 is a top view of the bayonet latching mechanisms of the two types shown in FIGS. 9 and 10.

Any mechanism that can squeeze the lid 98 together with the cup 90 so as to pinch the plastic cup 92 between the beveled surface 102 and the inside wall of the cup 90 will suffice for purposes of practicing the invention. One such alternative embodiment is shown in FIG. 10. Another such alternative embodiment is shown in FIG. 11.

Referring to FIG. 10 there is shown an alternative form of bayonet type sealing mechanism. In this embodiment, a latch lever 150 is rotatably coupled to the lid 152 by a pin coupling 154. When the lid 152 is in the unlatched position, the lever 150 is positioned vertically so that the centerline 156 is parallel with the z axis. This places the surface 158 parallel to the x axis and to the surface 160 of the flange 114 of the cup. The lever 150 has a latching cam 161 attached to the end thereof. This latching cam 161 has a camming surface 162 on it, and is attached to the lever 150 in such a way that the camming surface 162 engages the undersurface of the flange 114 when the lever 150 is rotated. That is, when the lever 150 is rotated counterclockwise from the vertical position and moved to the horizontal position with the centerline 156 parallel to the x axis, the lid 152 will be sealed to the cup 90. This occurs because the camming surface 162 engages the underside of the flange 114 and pushes the cup 90 upward into the lid 152 as the lever 150 is rotated counterclockwise. Once in this position, a constant force represented by the vector 126 is applied by a pneumatic piston 157 to the lever 150 to maintain the lid 152 and the cup 90 in sealed relationship. The force exerted by the camming surface 162 on the underside of the flange 114 tends to pinch the cup 90 and the lid 152 together. This causes the plastic cup 92 to be pinched between a beveled surface 102 on a cylindrical plateau 100 on the underside of the lid 152 and the inside wall of the stainless steel cup 90.

The force 126 can be applied by any mechanism. However, if it is desired to allow the cup to vent pressure when the pressure rises above a predetermined level, it is preferred to use the structure of FIG. 10 for the cup sealing mechanism. This safeguard prevents excessive pressure from building up in the cup. Venting action is automatic in the embodiment of FIG. 10 by using a pneumatic piston to apply the constant force 126. Then when pressure in the cup 92 rises to a sufficient level, the cup 92 and stainless steel cup 90 tend to move away from the lid 152 under the influence of the high pressure. This creates a downward force on the camming surface 162 through the flange 114 which tends to cause the lever 150 to rotate in the clockwise direction. When the pressure reaches a high enough level, the force tending to rotate the lever 150 clockwise is sufficient to overcome the constant force 126. In such a case, the lid 152 and the cup 90 separate slightly thereby venting the excess pressure. As soon as adequate pressure is vented, the force 126 tends to force the cup 90 and lid 152 into sealing engagement once again.

In the preferred embodiment, the cup 92 is made of translucent or transparent plastic such that the level of sample material in said cup may be seen. Further, the stainless steel cup or cup support means 90 has slots cut in it so that the cup 92 may be seen.

In alternative embodiments, the bayonet latching mechanisms may be replaced by screw on lids to pinch the plastic cup between the beveled surface and the inside wall of the cup support means. Such embodiments use threads on the outside of the stainless steel cup 90.

Although the invention has been described in terms of the preferred embodiment and alternative embodiments disclosed herein, those skilled in the art will appreciate other embodiments which accomplish the same result and which do not depart from the spirit of the invention. All such alternative embodiments are intended to be included within the scope of the claims appended hereto.

What is claimed is:

1. A sample preparation chamber for allowing samples of different compositions to be prepared for assay including a container having a bottom with at least one lowest region which is lower than all other regions in said bottom, said bottom having a configuration that tends to cause gravity to drive sample in said container to said at least one lowest region, comprising:

means insertable into said container for mixing non-homogeneous mixtures;

a fill/empty tube entering said container and having an inlet/outlet port located at said at least one lowest region; and sample metering means coupled to said container for isolating a known volume of sample from sample in said container and for allowing the known volume of sample to be released back into said container;

wherein said container comprises a first cup having a lip defining a first opening, a second cup for receiving said first cup and having a flange defining a second opening and further having means for receiving said lip onto said flange, and a cap having an edge for compression against said lip for sealing said first opening; and wherein said sample preparation chamber further comprises means for latching said cap against said first cup and said second cup, including a latch piece disposed adjacent said flange and said cap and having a notch for receiving said edge of said cap and said flange of said second cup, and a camming lever for compressing said cap edge against said flange and for compressing said lip of said first cup against said lip receiving means of said flange, with said camming lever rotatably carried by said latch piece and including a cam for contacting at least one of said cap edge and said flange of said second cup when said edge and said flange are positioned within said notch of said latch piece, where said cam is configured for compressing said cap edge against said flange of said second cup upon rotation of said camming lever.

2. The apparatus of claim 1, wherein said container has walls, and wherein the chamber further comprises a means for introducing liquids into said first cup having means for spraying the liquids against said walls of said first cup as the liquids are introduced into said first cup.

3. The apparatus of claim 1 further comprising a fill pipe means having an output port located in said first cup but displaced up from the bottom of said first cup by a predetermined clearance for allowing liquid to be introduced into said first cup.

4. The apparatus of claim 3 wherein said fill pipe means has a smaller diameter than said fill/empty tube.

5. An apparatus as defined in claim 1, further comprising means for aligning said latching means with said cap edge and said flange.

6. An apparatus as defined in claim 5, wherein said aligning means includes at least one pin carried on said cap and means defining at least one hole through said latch piece for receiving said at least me pin.

7. An apparatus as defined in claim 1, further comprising a piston mounted adjacent said camming lever and having an end contacting said camming lever for exerting a force against said lever, wherein the amount of force is selected for allowing said piston to be compressed when pressure in said first cup exceeds a predetermined amount, such that said pressure is vented through a gap formed between said flange and said edge, for automatically lowering said pressure to said predetermined amount.

8. The apparatus of claim 7 wherein said container has walls, and wherein the chamber further comprises means for introducing liquids into said first cup and having means for spraying the liquids against the walls of said first cup as the liquids are introduced into said first cup.

9. The apparatus of claim 8 further comprising a fill pipe means having an output port located in said first cup but displaced up from the bottom of said first cup by a predetermined clearance for allowing liquid to be introduced into said first cup.

10. The apparatus of claim 9 wherein said means for mixing includes means for grinding solid samples into smaller pieces.

11. A sample preparation chamber for allowing samples of different compositions to be prepared including a container comprising a cap and a chemically inert first cup having walls and a bottom with at least one lowest region, said bottom having a configuration that tends to cause gravity to drive sample in said container to said at least one lowest region, comprising:

means insertable into said container for mixing non-homogeneous fluids and for grinding samples into smaller pieces;

a fill/empty tube having a first diameter entering said container and having an inlet/outlet port located at said at least one lowest region;

sample metering means coupled to said container for isolating a known volume of sample from sample in said cup and for allowing the known volume of sample to be released back into said container; and means disposed within said cup for spraying said walls of said cup with liquids;

wherein said first cup includes a lip defining a first opening and said container further comprises a second cup for receiving said first cup and having a flange defining a second opening and further having means for receiving said lip of said first cup, and wherein said cap includes an edge for compression against said lip for sealing said first opening; and wherein said sample preparation chamber further comprises means for latching said cap against said first cup and said second cup, including a latch piece disposed adjacent said flange of said second cup and said cap and having a notch for receiving said edge of said cap and said flange, and a camming lever for compressing said cap edge against said flange and for compressing said lip of said first cup against said lip receiving means, with said camming lever rotatably carried by said latch piece and including a cam for contacting at least one of said cap edge and said flange of said second cup when said edge and said flange are positioned within said notch, where said cam is configured for compressing said cap edge against said flange of said second cup upon rotation of said camming lever.

12. The apparatus of claim 11 wherein said first cup is made of a material which is lightweight and allows light to pass therethrough.

13. The apparatus of claim 11 wherein said sample metering means comprises:
    means for allowing a sample to enter a chamber of a known volume;
    means for isolating said chamber of a known volume from the surrounding environment after the sample has been loaded therein;
    sealing means in said means for isolating to isolate the sample in said chamber without entrapping an unknown volume of sample in the sealing means.

14. The apparatus of claim 11 wherein said sample metering means comprises:
    a piston having a sample chamber formed therein as a cavity formed in a side of the piston, said cavity having a known volume;
    a cylinder enclosing said piston such that the piston may slide therein, said cylinder having means defining an aperture therein through which said piston may slide so as to expose said cavity to the environment outside said cylinder;
    means for forming a flush seal between said piston and said cylinder.

15. The apparatus of claim 11 wherein said sample metering means comprises:
    means for pumping predetermined amounts of liquid into or out of means defining a first system port;
    means for supplying pressurized gas or liquid to means defining a second system port;
    a container for storing sample and diluted sample;
    valve means for allowing said pumping means to pump sample out of said container into a sample chamber which may be selectively coupled to either said first or said second system port and for allowing sample in said sample chamber to be isolated from said container and both said first and second system ports and for allowing sample in said sample chamber to be placed back into said container.

16. The apparatus of claim 15 wherein control means causes said means for supplying pressurized gas or liquid to pressurize sample in said sample chamber before it is isolated in such a way as to minimize volume occupied by gas bubbles in said sample chamber.

* * * * *